United States Patent [19]
Josel et al.

[11] Patent Number: 5,958,783
[45] Date of Patent: *Sep. 28, 1999

[54] METAL COMPLEXES WITH A CHARGED LINKER

[75] Inventors: Hans-Peter Josel, Weilheim; Eva Höss, Starnberg; Beatus Ofenloch-Hähnle, Wielenbach; Christoph Seidel, Weilheim; Barbara Upmeier, Iffeldorf; Ursula-Henrike Wienhues, Krailling, all of Germany

[73] Assignee: Roche Diagnostics GmbH, Mannheim, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/615,278
[22] PCT Filed: Jul. 24, 1995
[86] PCT No.: PCT/EP95/02920
  § 371 Date: Jun. 20, 1996
  § 102(e) Date: Jun. 20, 1996
[87] PCT Pub. No.: WO96/03409
  PCT Pub. Date: Feb. 8, 1996

[30] Foreign Application Priority Data

Jul. 25, 1994 [DE] Germany ............... 44 26 276
Aug. 31, 1994 [DE] Germany ............... 44 30 998
Nov. 4, 1994 [DE] Germany ............... 44 39 347
Nov. 4, 1994 [DE] Germany ............... 44 39 345

[51] Int. Cl.$^6$ ............ G01N 33/20; G01N 21/76; C07F 15/00; C09K 11/06
[52] U.S. Cl. ............ 436/84; 436/518; 436/172; 436/536; 436/537; 556/136; 252/301.16; 252/301.33; 546/10
[58] Field of Search ............ 436/172, 518, 436/800, 84, 92, 546, 536, 537; 556/136; 252/301.16, 301.33, 301.4 R; 546/10

[56] References Cited

U.S. PATENT DOCUMENTS 4,745,076  5/1988  Muller et al. ............... 436/557
5,075,447  12/1991  Muller et al. ............... 546/10

OTHER PUBLICATIONS

Terpetschnig et al., Biophysical journal., vol. 68., pp. 342–350, Jan. 1995.
International Patent Application No. WO 86/02734 published May 9, 1986.

Primary Examiner—Ponnathapura Achutamurthy
Assistant Examiner—P. Ponnaluri
Attorney, Agent, or Firm—Nikaido Marmelstein Murray & Oram, LLP.

[57] ABSTRACT

The present invention concerns new metal complexes with a charged linker and their use as luminescent marker groups in an immunoassay.

35 Claims, 3 Drawing Sheets

```
                        SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: Modified with an acetyl group and a
      ruthenium(bipridyl) complex
<220> FEATURE:
<221> NAME/KEY: MOD_RES
<222> LOCATION: (2)
<223> OTHER INFORMATION: Xaa is Fmoc-B alanine-OH
<220> FEATURE:
<221> NAME/KEY: MOD_RES
<222> LOCATION: (4)
<223> OTHER INFORMATION: Xaa is Fmoc-B alanine-OH
<220> FEATURE:
<221> NAME/KEY: MOD_RES
<222> LOCATION: (6)
<223> OTHER INFORMATION: Xaa is Fmoc-B alanine-OH
<220> FEATURE:
<221> NAME/KEY: MOD_RES
<222> LOCATION: (7)
<223> OTHER INFORMATION: Modified with a acid-bis-N-hydroxysuccinimide
      ester (DSS)
<220> FEATURE:
<221> NAME/KEY: MOD_RES
<222> LOCATION: (8)
<223> OTHER INFORMATION: Xaa is Fmoc-B alanine-OH
<220> FEATURE:
<221> NAME/KEY: MOD_RES
<222> LOCATION: (10)
<223> OTHER INFORMATION: Xaa is Fmoc-B alanine-OH
<220> FEATURE:
<221> NAME/KEY: MOD_RES
<222> LOCATION: (12)
<223> OTHER INFORMATION: Xaa is Fmoc-B alanine-OH
<220> FEATURE:
<221> NAME/KEY: MOD_RES
<222> LOCATION: (13)
<223> OTHER INFORMATION: Modified with a ruthenium(bipridyl) complex
<220> FEATURE:
<221> NAME/KEY: MOD_RES
<222> LOCATION: (14)
<223> OTHER INFORMATION: Xaa is Fmoc-B alanine-OH
<220> FEATURE:
<223> OTHER INFORMATION: Description of Artificial Sequence: Peptide
      Derivative

<400> SEQUENCE: 1

Lys Xaa Glu Xaa Glu Xaa Lys Xaa Glu Xaa Glu Xaa Lys Xaa Glu
 1               5                  10                  15
```

METAL COMPLEXES WITH A CHARGED LINKER

This application is a 371 of PCT/EP95/02920 filed Jul. 24, 1995.

DESCRIPTION

The present invention concerns new metal complexes with a charged linker and their use as luminescent marker groups in immunoassays.

Luminescent metal complexes are known from the state of the art. EP-A-0 178 450 discloses ruthenium complexes that are coupled to an immunologically active material in which the ruthenium complexes contain three identical or different bicyclic or polycyclic ligands with at least two nitrogen-containing heterocycles and at least one of these ligands is substituted with at least one water-solubilizing group such as —$SO_3H$ or —COOH and at least one of these ligands is substituted directly or via a spacer group with at least one reactive group and the ligands are bound via nitrogen atoms to the ruthenium.

The groups capable of coupling are introduced in a very complicated manner by activation and consecutive reactions on the solubilizing groups of the ligands. The production of monoactivated compounds which enable coupling to biological substances such as antibodies without cross-linking also proves to be particularly complicated.

EP-A-0 580 979 discloses the use of osmium and ruthenium complexes as marker groups for electrochemiluminescence. Heterocycles containing nitrogen such as bipyridines are mentioned as ligands for these complexes. WO 87/06706 discloses further metal complexes which are suitable as marker groups for electrochemiluminescence measurements.

Further disadvantages of the known metal complexes of the state of the art are a poor quantum yield in electrochemiluminescence measurements due to oxygen quenching and photodissociation or/and a high unspecific binding to proteins.

Therefore the object underlying the present invention was to at least partially eliminate the disadvantages of the state of the art.

Surprisingly it was found that the introduction of free positive or/and negative charge carriers into the linker which links the reactive coupling group of the metal complex to one of the ligands reduces the adsorption of conjugates of these complexes with an immunologically reactive substance and thus also improves the stability and recovery of the conjugates in immunoassays. Moreover an increased quantum yield can be achieved.

Furthermore it was found that luminescent metal complexes with a charged linker can be produced in a surprisingly simple manner.

One subject matter of the present invention is thus a metal complex of the general formula (I):

$$[M(L_1L_2L_3)]_n\text{-}X_m\,A \qquad (I)$$

in which M is a divalent or trivalent metal cation selected from rare earth or transition metal ions, $L_1$, $L_2$ and $L_3$ are the same or different and denote ligands with at least two nitrogen-containing heterocycles wherein $L_1$, $L_2$ and $L_3$ are bound to the metal cation via nitrogen atoms, X is a reactive functional group which is covalently bound to at least one of the ligands $L_1$, $L_2$ and $L_3$, n is an integer from 1 to 10, m is an integer from 1 to 6 and is preferably 1 to 3 and A denotes the counterions which may be required to balance the charge wherein the linker contains at least one positive or/and negative charge carrier.

DESCRIPTION OF THE PREFERRED EMBODIMENTS

Figure 1:
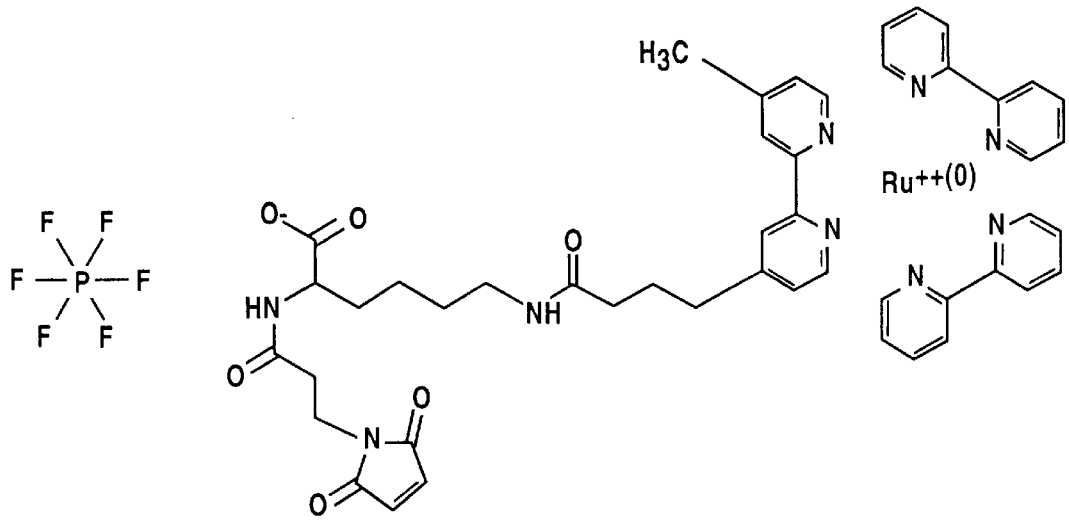
FIGS. 1–5 show preferred compounds of the present invention.

The metal complex is preferably a luminescent metal complex i.e. a metal complex which can generate a detectable luminescence reaction. This luminescence reaction can for example be detected by fluorescence or by electrochemiluminescence measurement. The metal cation in this complex is for example a transition metal or a rare earth metal. The metal is preferably ruthenium, osmium, rhenium, iridium, rhodium, platinum, indium, palladium, molybdenum, technetium, copper, chromium or tungsten. Ruthenium, iridium, rhenium, chromium and osmium are particularly preferred. Ruthenium is most preferred.

The ligands $L_1$, $L_2$ and $L_3$ are ligands containing at least two nitrogen-containing heterocycles. Aromatic heterocycles are preferred such as bipyridiyl, bipyrazyl, terpyridyl and phenanthrolyl. The ligands $L_1$, $L_2$ and $L_3$ are preferably selected from bipyridine and phenanthroline ring systems.

The reactive functional group X of the complex is a reactive group that can be coupled to an immunological active substance. The group X is preferably an activated carboxylic acid group such as a carboxylic acid halogenide, a carboxylic acid anhydride or an active ester e.g. an N-hydroxysuccinimide ester, p-nitrophenyl ester, pentafluorophenyl ester, imidazolyl ester or N-hydroxybenzotriazolyl ester a maleimide or a group which can be photoactivated e.g. an azide. The complex preferably contains only a single functional group X.

In addition the complex can optionally contain one or several counterions A to balance the charge. Examples of suitable negatively charged counterions are halogenides, $OH^-$, carbonate, alkyl carboxylate e.g. trifluoroacetate, sulfate, hexafluorophosphate and tetrafluoroborate groups. Hexafluorophosphate, trifluoroacetate and tetrafluoroborate groups are particularly preferred. Examples of suitable positively charged counterions are monovalent cations such as alkali metal and ammonium ions.

The metal complex according to the invention differs from the metal complexes known from the state of the art in that it contains at least one charge carrier in the linker between the ligand and the reactive group X capable of coupling. The term "charge carrier" denotes within the sense of the present invention a group which is present mainly in an ionic form at a pH value in the range 6–8. The linker preferably contains up to 10, particularly preferably 2–8 and most preferably 2–4 such charge carriers.

The linker particularly preferably contains at least one negative charge carrier. Examples of suitable negative charge carriers are phosphate, phosphonate, sulfonate and carboxylate groups, of which carboxylate groups are most preferred.

Examples of positive charge carriers are amino groups and singly or multiply substituted amino groups such as mono, di or trialkyl amino groups in which alkyl denotes a straight-chained or branched alkyl residue of 1–6 C atoms or a cyclic alkyl residue of 3–6 C atoms. The positive charge carriers are particularly preferably selected from basic amino acids such as lysine or substituted amino acids such as diethyllysine. Amines and substituted amines can also serve as electron donors in the detection of the metal complexes by electrochemiluminescence.

The linker preferably has a chain length of 4–40 atoms and is an alkylene chain modified by the incorporation of heteroatoms such as amide functions. The charge carriers are preferably arranged in the linker in such a way that an H atom of an alkylene unit is replaced by a charged group e.g. $NH_2^+$ or $CO_2^-$.

The linker which contains the free charge carriers is preferably composed at least partially of amino-carboxylic acid units which are linked together via peptide bonds. In such a linker the charge carriers can be derived from free amino or/and carboxylate groups of polyfunctional aminocarboxylic acids which contain a total of at least three charged groups (amino plus carboxylate) so that after incorporation into the linker and the concomitant reaction of two of the charged groups at least one free charge carrier is still present. For example the charge carriers can be derived from trifunctional aminocarboxylic acids which contain (a) an amino group and two carboxylate groups or (b) two amino groups and one carboxylate group. Examples of such trifunctional aminocarboxylic acids are lysine, ornithine, hydrolxylysine, aspartic acid and glutamic acid.

The metal complex according to the invention can additionally contain at least one hydrophilic group selected from $C_2$–$C_3$ alkylenoxy units, $C_2$–$C_3$ alkylenethio units, $C_2$–$C_3$ alkylenamino units and polyhydroxy units.

The polyhydroxy units are preferably selected from groups of formulae (IIa) or (IIb):

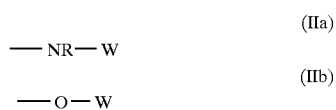

in which W denotes an organic residue with at least two hydroxy groups and R denotes hydrogen or $C_1$–$C_5$ alkyl. The organic residue W preferably contains 2 to 6 and particularly preferably 2 to 4 hydroxy groups. Furthermore W should advantageously contain 2 to 10 and in particular 3–6 carbon atoms. Specific examples of suitable polyhydroxy units are residues of polyalcohols such as glycerol or aminopolyalcohols. A preferred aminopolyalcohol is Tris (2-amino-2-(hydroxymethyl)-1,3-propanetriol). In this case the polyhydroxy unit has the formula $NH—C(CH_2OH)_3$. The polyalcohols or aminopolyalcohols are preferably coupled to the metal complex in the form of esters or amides. The OH groups of the polyalcohol or aminopolyalcohols can be optionally substituted by hydrophilic groups e.g. by dendrimeric groups.

The $C_2$–$C_3$ alkylenoxy, $C_2$–$C_3$-alkylenethio and $C_2$–$C_3$-alkylenamino units of the metal complex according to the invention are preferably $C_2$ units and in particular ethylenoxy units. The complex preferably contains 1 to 30 and particularly preferably 2 to 20 $C_2$–$C_3$ alkylenoxy, $C_2$–$C_3$ alkylenethio or $C_2$–$C_3$ alkylenamino units per metal cation. These units are components of substituents of the heterocyclic ligands of the metal complex. They can be present in the linker between one of the ligands and the reactive functional group X or/and in monosubstituents. The alkylenoxy, alkylenethio or alkylenamino units can also be linked together via a bridgehead which can optionally carry a functional group X. On the other hand several complex units can also be linked together via the bridgehead.

In one embodiment of the present invention the metal complex according to the invention has the general formula (III):

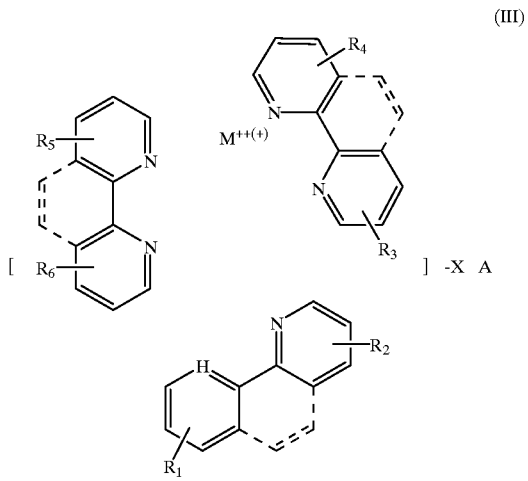

in which M, X and A are defined as above, $R_1$, $R_2$, $R_3$, $R_4$, $R_5$ and $R_6$ are the same or different and each denotes one or several substituents provided that X is linked to one of the ligands via one of the substituents $R_1$, $R_2$, $R_3$, $R_4$, $R_5$ and $R_6$ as the linker.

The ligands of the complex may also be substituted phenanthroline or bipyridine systems depending on the presence or absence of the groups indicated by the broken lines.

The substituents $R_1$, $R_2$, $R_3$, $R_4$, $R_5$ and $R_6$ on the ligand are—provided they do not contain the group X of the linker—preferably hydrogen, $C_1$–$C_5$ alkyl and in particular $C_1$–$C_3$ alkyl or a hydrophilic group as defined above.

In a particularly preferred embodiment the metal complexes have the general formula (IIIa):

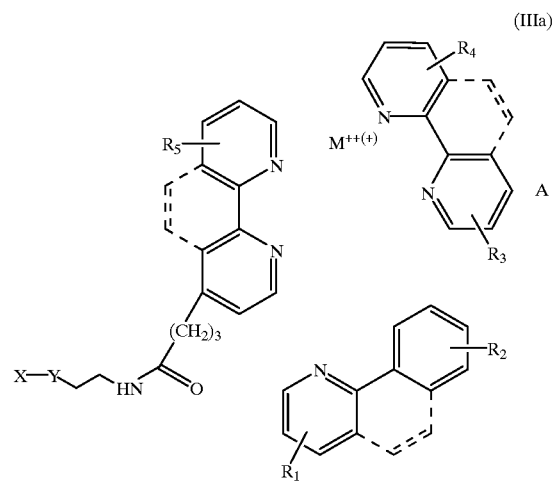

in which M, X and A are defined as above, $R_1$, $R_2$, $R_3$, $R_4$ and $R_5$ are defined as above, s is an integer from 0 to 6 and preferably from 1 to 4 and Y denotes the linker with free charge carriers.

Figure 2:
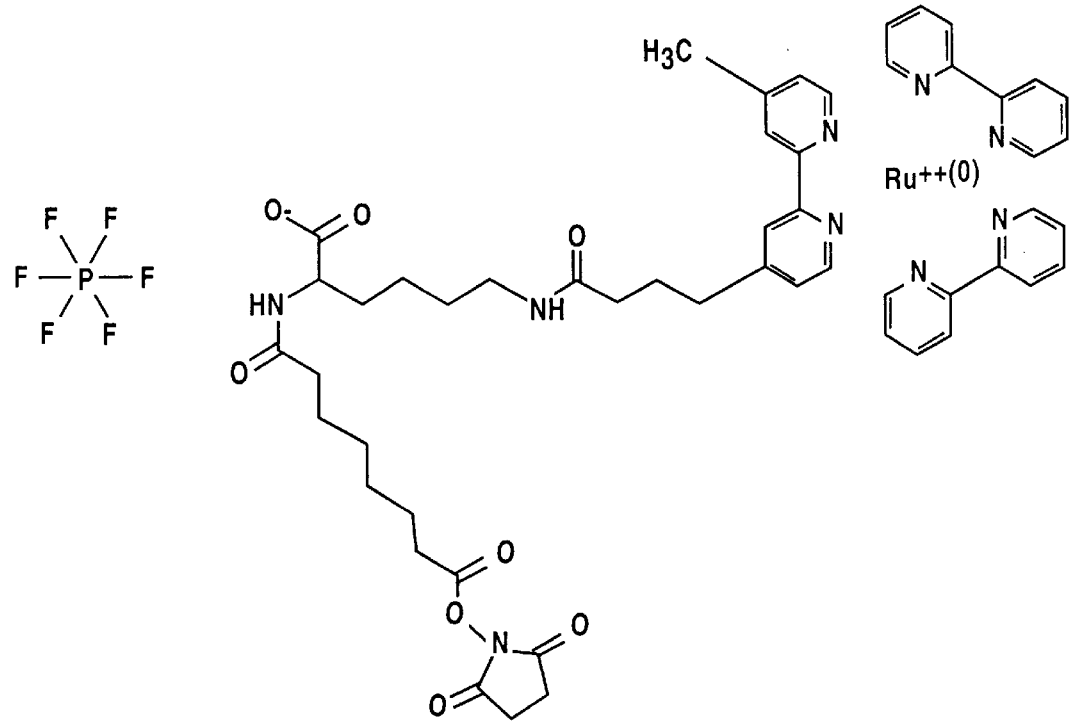
Figure 3:
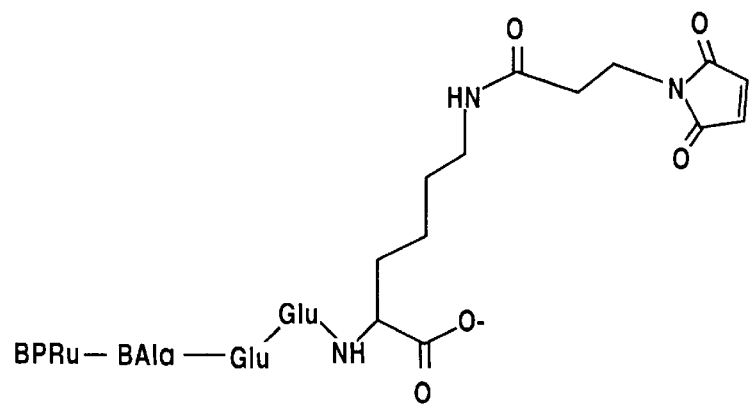

Examples of compounds of formulae (III) and (IIIa) are shown in FIGS. 1–3. FIGS. 1 and 2 show complexes which have a linker with one free negative charge carrier in each case. In each case the linker contains a trifunctional amino acid, namely lysine, whose amino groups serve to form peptide bonds in the linker whereas the carboxylate group forms the free charge carrier. FIG. 3 shows a linker composed of 4 amino acid units namely β-alanine, lysine and two glutamic acid residues.

The linker contains three negative charge carriers, one carboxylate group from each of the two Glu residues and one carboxylate group which is derived from Lys. The functional group X in FIGS. 1 and 3 is a maleimide suitable for coupling to SH groups and in FIG. 2 it is an N-hydroxysuccinimide ester suitable for coupling to $NH_2$ groups.

The ligands of the metal complex according to the invention can also be linked together so that the metal complex is present in the form of a semicage or cage. A preferred embodiment of a metal complex according to the invention in the form of a semicage or cage has the general formula (IV):

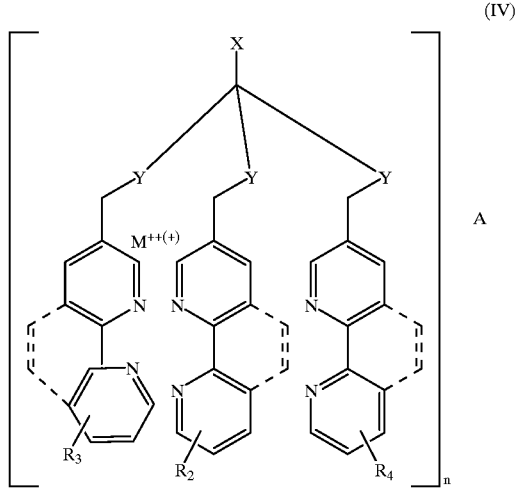

in which M, X, n and A are defined as above, $R_1$, $R_2$ and $R_3$ are the same or different and each denote one or several substituents—as defined above—on the bipyridine or phenanthroline ligand and Y in each case denotes a linker with at least one charge carrier.

If the substituents $R_1$, $R_2$ and $R_3$ in formula (IV) are covalently linked together optionally via linker groups, then the complex of formula (IV) is in the form of a cage.

The complex of formula (IV) may not only be present as a monomer but as an oligomer composed of preferably up to 5 individual metal complexes. In this case the functional group X capable of coupling can for example be a substituent on an aromatic nucleus. e.g. a phenyl nucleus in which case two or several of the remaining substituent positions of the aromatic nucleus can be substituted by a metal complex in the form of a semicage or cage.

The metal complexes according to the invention can be produced by reacting a metal salt e.g. a metal halogenide with the appropriate ligands and optionally subsequently replacing the halogenide ion by hexafluorophosphate, trifluoroacetate or tetrafluoroborate anions. Such processes are described in the state of the art e.g. in U.S. Pat. No. 4,745,076, U.S. Pat. No. 5,075,447 and U.S. Pat. No. 5,585,279. Reference is hereby made to this disclosure.

The synthesis of a charged linker on an N-heterocyclic ligand with a charged linker can on the one hand be achieved as a coupling reaction in solution in which an optionally partially protected aminocarboxylic acid is coupled to a reactive group of the ligand e.g. a carboxylic acid. This coupling section can if necessary be repeated again until a linker of the desired length has been synthesized. In this process at least one polyfunctional aminocarboxylic acid group is introduced which contains one or several charged side groups.

Subsequently the reactive group X is introduced and protecting groups which may be present on the side groups of the aminocarboxylic acids are cleaved off. This synthesis of the ligand by successive coupling of amino acids in solution can on the one hand be carried out on a single ligand and, on the other hand, on a ligand as starting material which is already bound to a metal complex. A suitable starting material is for example a luminescent metal complex which contains a free carboxylate group. Such complexes are known from the above-mentioned documents and are commercially available for example from Igen Inc. Co., Rockville, Md., USA.

On the other hand the complexes can also be synthesized by solid phase peptide synthesis. In a first embodiment of the solid phase synthesis an amino acid is coupled to the solid phase support via its carboxylate group and the desired linker is then synthesized by successive coupling of further amino acids. In order to produce a linker according to the invention at least one amino acid is used in this process which contains a charged group as a side group e.g. an amino or carboxylate group, optionally in a protected form. After the desired linker sequence has been completed, an activated metal complex e.g. in the form of an active ester, can be coupled to the free N-terminal amino group of the solid phase-bound peptide. After cleavage from the solid phase the reactive group X can be coupled to the carboxy terminus of the peptide linker and protecting groups which may be present are cleaved.

In another embodiment of the solid phase synthesis an amino acid-metal complex conjugate which contains a protected amino group and a carboxylate group e.g. Fmoc-Lys (BRu)—OH (FIG. 4), can be anchored to a solid phase via the free carboxylate group and a peptide linker can be synthesized after releasing the blocked amino group. After finishing the desired linker sequence the complex is cleaved from the solid phase to obtain a linker which contains at least the original carboxylate anchor group as the free charge carrier. The reactive group X can be coupled to the amino terminus of the resulting peptide linker.

In a third embodiment of the solid phase synthesis the linker sequence with charge carriers can also be synthesized directly on a selected peptide epitope.

A combination of the above-mentioned synthesis variants can also be used to produce the metal complexes according to the invention. Amino acid-metal complex conjugates that are suitable for the solid phase synthesis of the complexes according to the invention with a charged linker are described in DE-A-44 30 998.8. Reference is hereby made to this disclosure.

The production of metal complexes of formula (IV) with a semicage or cage structure can for example be carried out by attaching charged linkers to the bipyridine or phenanthroline ligands and linking these units to a bridgehead via an amide bond. If two bridgeheads are used it is possible to obtain complete cage structures. The linking of three ligands to a trivalent bridgehead e.g. Tris is preferred.

A further subject matter of the present invention is a conjugate comprising a biological substance to which at least one metal complex according to the invention is coupled. Examples of suitable biological substances are cells, viruses, subcellular particles, proteins, lipoproteins, glycoproteins, peptides, polypeptides, nucleic acids, peptidic nucleic acids (PNA), oligosaccharides, polysaccharides, lipopolysaccharides, cellular metabolites, haptens, hormones, pharmacologically active substances, alkaloids, steroids, vitamins, amino acids and sugars.

The metal complex is coupled to the biological substance via the reactive functional group of the metal complex which can covalently couple to a functional group of the biological substance. If the functional group is an active ester it can for example be coupled to the free amino groups of the biological substance. If the functional group is a maleinimide residue it can be coupled to the free SH groups of the biological substance.

In a particularly preferred embodiment of the present invention the metal complexes are coupled to a peptide which preferably has a maximum length of 50 amino acids and particularly preferably of 30 amino acids. The production of these peptides labelled with a metal complex is preferably carried out by synthesizing a peptide with the desired amino acid sequence on a solid phase in which a) after the synthesis an activated metal complex, preferably a metal complex-active ester derivative, is coupled to the N-terminal amino group of the peptide or/and b) during the synthesis an amino acid derivative that is covalently coupled to a metal complex is introduced in at least one position of the peptide. The coupling of the metal complex to the N-terminal amino acid of the peptide is preferably carried out before cleaving the peptide from the solid phase and before cleaving protecting groups on reactive side groups of the amino acid derivatives used for the peptide synthesis.

The peptides preferably contain an immunologically reactive epitope region and a spacer region wherein at least one metal complex marker group is coupled to the spacer region. The spacer region preferably has a length of 1 to 10 amino acids and is located at the amino or/and carboxy terminus of the peptide.

The spacer region preferably contains amino acids which have charges or/and can form hydrogen bridges. The amino acids of the spacer region are preferably formed from the group comprising glycine, β-alanine, γ-aminobutyric acid, ε-aminocaproic acid, lysine and compounds of the structural formula $NH_2-[(CH_2)_yO]_x-CH_2-CH_2-COOH$ in which y is 2 or 3 and x is 1 to 10.

The epitope regions of the peptides are preferably derived from pathogenic organisms e.g. bacteria, viruses and protozoa or from autoimmune antigens. The epitope region is particularly preferably derived from viral antigens e.g. the amino acid sequences of HIVI, HIVII or hepatitis C virus (HCV).

Further preferred examples of biological substances are biotin, nucleic acids, antibodies or antibody fragments, polypeptide antigens i.e. immunologically reactive polypeptides or haptens i.e. organic molecules with a molecular weight of 150 to 2000, in particular molecules with a steroid backbone such as cardenolides, cardenolide-glycosides (e.g. digoxin, digoxigenin), steroid alkaloids, sexual hormones (e.g. progesterone), glucocorticoids etc. Further examples of haptens are prostaglandins, leucotrienes, leuco-en-diines, thromboxanes etc.

Yet a further subject matter of the present invention is the use of the metal complexes according to the invention or of the conjugates according to the invention in an immunological detection method or a nucleic acid hybridization method, in particular in a luminescence assay.

In these methods the metal complex is used as a marker group with the aid of which it is possible to qualitatively or/and quantitatively determine an analyte in a sample solution. The metal complex is preferably detected by electrochemiluminescence in which case luminescent species are generated electrochemically on the surface of an electrode. Examples for carrying out luminescence assays using metal complexes from the state of the art may be found in EP-A-0 580 979, WO 90/05301, WO 90/11511 and WO 92/14138. Reference is hereby made to the methods and devices for luminescence assays disclosed therein. Electrochemiluminescence assays are carried out in the presence of a solid phase which is preferably composed of microparticles and in particular of magnetic microparticles which are provided with a reactive coating e.g. with streptavidin. In this manner immune or hybridization complexes containing a metal complex as a marker group can be detected bound to a solid phase.

The electrochemiluminescence measurement is preferably carried out in the presence of a reducing agent for the metal complex e.g. an amine. Aliphatic amines and in particular primary, secondary and tertiary alkylamines, the alkyl groups of which each have 1 to 3 carbon atoms are preferred. Tripropylamine is particularly preferred. The amine can, however, also be an aromatic amine such as aniline or a heterocyclic amine. The reducing agent can already be integrated into the ligand sphere of the complex.

In addition a non-ionic surface-active agent may also be present as an amplifier e.g. an ethoxylated phenol. Such substances are for example commercially available under the names Triton X100 or Triton N401.

On the other hand the luminescent metal complex can also be detected by fluorescence in which case the metal chelate is excited by irradiation with light of a suitable wavelength and the resulting fluorescent radiation is measured. Examples for carrying out fluorescence assays may be found in EP-A-0 178 450 and EP-A-0 255 534. Reference is hereby made to this disclosure.

The previously described principle of using metal complexes with charged linkers can in addition also be applied to other marker or/and solid phase binding groups. The present invention therefore also concerns marker or/and solid phase binding groups with a reactive functional group X covalently bound via a linker wherein the linker contains at least one positive or/and negative charge carrier. The linker is preferably composed at least partially of aminocarboxylic acid units which are linked together via peptide bonds.

The marker or/and solid phase binding groups are preferably selected from fluorescent marker groups such as e.g. fluorescein, coumarin, rhodamine, resorufin, cyanine and derivatives thereof as well as biotin and biotin analogues such as iminobiotin or desthiobiotin.

The invention also concerns conjugates of the aforementioned marker or/and solid phase binding groups with a biological substance as defined previously. The marker or/and solid phase binding groups or conjugates thereof can be used in an immunological detection method or in a nucleic acid hybridization method. In these methods it is possible to achieve an improvement in the solubility and a reduction or prevention of signal quenching due to the formation of dimers or higher aggregates.

Yet a further subject matter of the present invention is a process for introducing an N-hydroxysuccinimide ester group into peptides or peptide derivatives which is characterized in that a peptide or peptide derivative which has a free amino function, preferably an aliphatic and particularly preferably a primary aliphatic amino function, is reacted with suberic acid-bis-hydroxysuccinimide ester (DSS) thus converting the amino function into an N-hydroxysuccinimide ester. The peptide or peptide derivative activated by introducing the N-hydroxysuccinimide ester group can subsequently be coupled to biological substances as defined above.

A particular advantage of this process is that peptides or peptide derivatives can be used which have at least one free acid function and in particular a carboxylic acid function. In contrast to known processes it is not necessary to block the acid function.

In addition to peptides one can also activate those peptide derivatives which carry at least one marker or/and solid phase binding group e.g. a metal complex, a fluorescent group or a biotin group.

The activation reaction is preferably carried out in an organic solvent such as dimethylformamide in the presence of a base e.g. a tertiary amine such as triethylamine. The suberic acid-bis-N-hydroxysuccinimide ester is preferably used in a molar excess of 2:1 to 10:1 relative to the peptide or peptide derivative.

The present invention is further elucidated by the following examples and figures.

FIGS. 1–3 show metal complexes according to the invention

Figure 4:
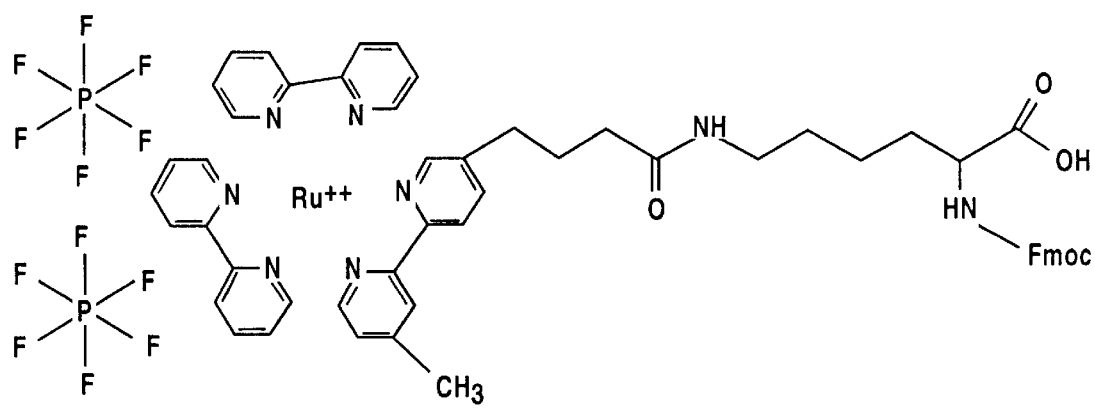
Figure 5:
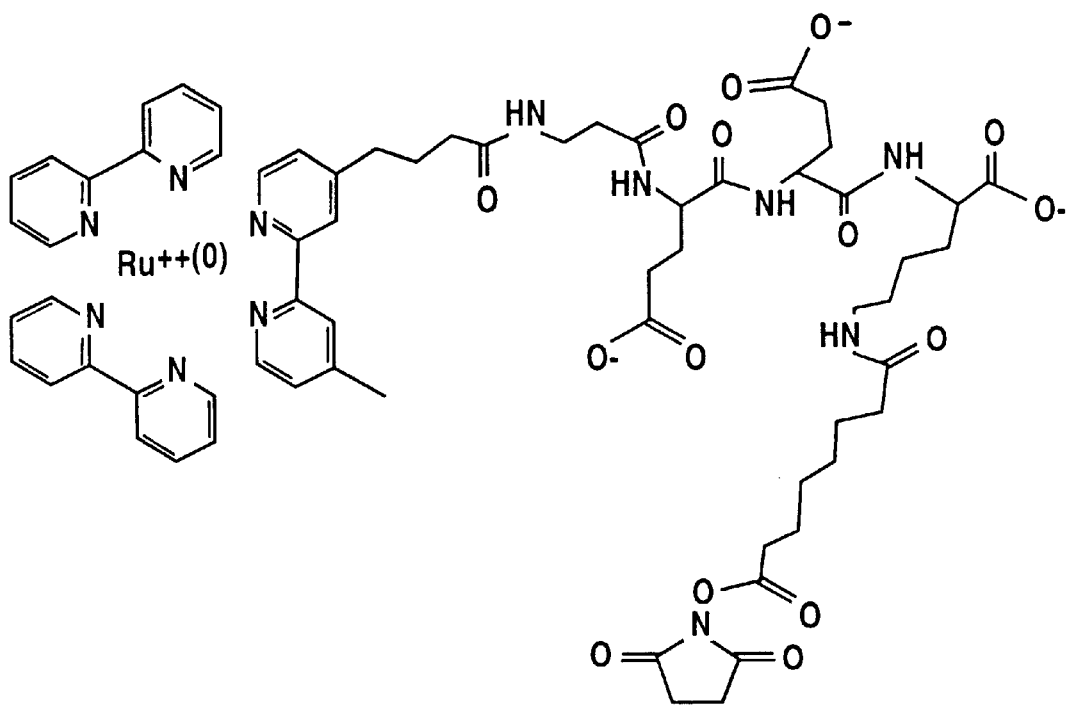

FIG. 4 shows an amino acid metal complex conjugate suitable for synthesizing a metal complex according to the invention and FIG. 5 shows an activated peptide-metal complex conjugate.

EXAMPLE 1

Production of a metal complex with a charged linker 6 mmol of the metal complex Ru(bipyridine)$_2$-(bipyridine-CO-N-hydroxysuccinimide ester) according to EP-A-0 580 979 is dissolved in 50 ml dimethylformamide and a solution of Fmoc-lysine in dimethylformamide is added dropwise. The solvent is removed in a high vacuum. The residue is dissolved in a small amount of acetone, admixed with 300 ml chloroform and briefly heated to boiling point. It is allowed to cool and the separated oil is separated from the solvent. The desired compound Ru(bpy)$_2$(bpy-CO-(Fmoc)-Lys) is obtained as a solid substance by drying.

The Fmoc protecting group is cleaved by reaction for 2 hours at 80° C. in dioxane/acetone in a 4-fold excess of piperidine. After cooling the oily residue is separated and a chloroform/water extraction is carried out. The aqueous phase is isolated and the compound Ru(bpy)$_2$(bpy-CO-Lys) is obtained as a red solid.

60 mg of this compound is dissolved in 10 ml acetone, maleimidopropionic acid-N-hydroxysuccinimide ester is added and it is stirred for 4 hours at room temperature. The residue is purified by preparative HPLC. 17 mg of the compound Ru(bpy)$_2$(bpy-CO-Lys-MP) is obtained. This compound is shown in FIG. 1.

EXAMPLE 2

Production of a metal complex with a charged linker

Ru(bpy)$_2$(bpy-CO-Lys) according to example 1 and a 10-fold molar excess of suberic-bis-N-hydroxysuccinimide ester are dissolved in dimethylformamide and stirred for 2 hours at room temperature. The solvent is removed in a high vacuum, the residue is extracted with water and lyophilized after treatment with hexane. It is purified by means of HPLC (100% H$_2$O, in 20 min to 100% acetonitrile, C$_{18}$, 3 μm column, flow rate: 1 ml/min, retention time: 10.00 min.). The compound obtained is shown in FIG. 2.

EXAMPLE 3

Production of metal complexes by means of solid phase peptide synthesis

The metal complexes with a charged linker were produced by means of fluorenylmethyloxycarbonyl-(Fmoc)-solid phase peptide synthesis on a batch peptide synthesizer e.g. from Applied Biosystems A431 or A433. For this 4.0 equivalents of the amino acid derivatives shown in Table 1 were used in each case.

TABLE 1

| | |
|---|---|
| A | Fmoc-Ala-OH |
| C | Fmoc-Cys(Trt)-OH |
| D | Fmoc-Asp(OtBu)-OH |
| E | Fmoc-Glu(OtBu)-OH |
| F | Fmoc-Phe-OH |
| G | Fmoc-Gly-OH |
| H | Fmoc-His(Trt)-OH |
| I | Fmoc-Ile-OH |
| K1 | Fmoc-Lys(Boc)-OH |
| K2 | Boc-Lys(Fmoc)-OH |
| K3 | Fmoc-Lys(BPRu)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pmc)-OH |
| S | Fmoc-Ser(tBu)-OH |
| T | Fmoc-Thr(tBu)-OH |
| U | Fmoc-Balanine-OH |
| V | Fmoc-Val-OH |
| W | Fmoc-Trp-OH |
| Y | Fmoc-Tyr(tBu)-OH |
| Z | Fmoc-ε-aminocaproic acid-OH |
| Nle | Fmoc-ε-norleucine-OH |
| Abu | Fmoc-γ-aminobutyric acid-OH |

In the variant (a)—introduction of the metal complex after completion of the solid phase synthesis—an activated ruthenium(bipyridyl)$_3$ complex (BPRu) e.g. Ru(bpy)$_2$(bpy-CO-NHS) (cf. example 1) was coupled to the N-terminal amino acid of the peptide.

According to variant (b) metal chelate groups were introduced into the peptide sequence by direct incorporation of metal chelate-coupled amino acid derivatives e.g. at the carboxyl terminus of the sequence via a lysine residue ε-derivatized with a metal chelate active ester e.g. the lysine derivative K3 (FIG. 4).

The amino acids or amino acid derivatives were dissolved in N-methylpyrrolidone. The peptide was synthesized on 400–500 mg (4-(2',4'-dimethoxyphenyl-Fmoc-aminomethyl)-phenoxy resin (Tetrahedron Letters 28 (1987), 2107) loaded with 0.4–0.7 mmol/g (JACS 95 (1973), 1328). The coupling reactions were carried out for 20 min. with 4 equivalents dicyclohexylcarbodiimide and 4 equivalents N-hydroxybenzotriazole with respect to the Fmoc-amino acid derivative in dimethylformamide as the reaction medium. The Fmoc group was cleaved within 20 min. after each synthesis step using 20% piperidine in dimethylformamide.

When cysteine residues were present in the peptide sequence, the solid phase was oxidized immediately after completing the synthesis using iodine in hexafluoroisopropanol/dichloromethane.

The peptide was released from the support and the acid-labile protecting groups were cleaved using 20 ml trifluoroacetic acid, 0.5 ml ethanedithiol, 1 ml thioanisole, 1.5 g phenol and 1 ml water in 40 min. at room temperature. The reaction solution was subsequently admixed with 300 ml cooled diisopropyl ether and kept at 0° C. for 40 min. until complete precipitation of the peptide. The precipitate was filtered, rewashed with diisopropyl ether, dissolved in a small amount of 50% acetic acid and lyophilized. The crude material obtained was purified by means of preparative HPLC on Delta-PAK RP C18 material (column 50×300 mm, 100 Å, 15 μ) over a corresponding gradient (eluant A: water, 0.1% trifluoroacetic acid, eluant: B acetonitrile, 0.1% trifluoroacetic acid) in ca. 120 min. The identity of the eluted material was checked by means of ion spray mass spectrometry.

The metal chelate label was introduced on the free N-terminal amino group of the support-bound peptide according to variant (a) via appropriate active ester derivatives. For this 4 equivalents ruthenium (bipyridyl)$_3$ complex (BPRu) per free primary amino function were activated with N-hydroxybenzotriazole/dicyclohexylcarbodiimide, dissolved in a small amount of DMSO, added dropwise and stirred at room temperature. The reaction was monitored by means of analytical HPLC. After cleaving from the support, the product was purified by preparative HPLC. The identity of the eluted material was checked by means of ion spray mass spectrometry.

The peptides were synthesized by a combination of variant (a) and (b) i.e. incorporation of metal-chelate-coupled amino acid derivatives within the sequence, cleaving the N-terminal Fmoc group and reacting the free N-terminal amino group with a metal-chelate active ester derivative.

When the metal chelate-coupled amino acid derivatives were exclusively incorporated directly during the solid phase synthesis according to variant (b), it was no longer necessary to subsequently introduce metal chelate active esters.

An example of a metal complex produced by solid phase synthesis is shown in FIG. 3.

In order to introduce the maleinimide function the peptide was dissolved in 0.1 M potassium phosphate buffer pH 7.0 and admixed with one equivalent of maleinimide propionic acid-N-hydroxysuccinimide ester in DMSO and stirred for 16 hours at 25° C. The mixture was purified by means of preparative HPLC (see above). The identity of the eluted material was checked by means of ion spray mass spectrometry. A reactive N-hydroxysuccinimide ester function was introduced according to DE-A-43 02 241.

EXAMPLE 4

Use of metal complexes with a charged linker in immunological tests

A double-antigen bridge test was carried out to detect specific antibodies against hepatitis C virus (HCV). For this the sample liquid was incubated with a ruthenium-labelled antigen and a biotinylated antigen against the antibody to be determined in the presence of a solid phase coated with streptavidin. The presence of anti-HCV antibodies in the sample liquid was determined by determining the label in the solid phase by electrochemiluminescence according to the Flash system.

A HCV polypeptide was used as an antigen which contains the amino acids 1207–1488 of HCV. The amino acid sequence and the synthesis of such a polypeptide is described in DE-A-44 28 705.4.

In order to derivatize the HCV polypeptide with ruthenium complexes activated with succinimide ester, the polypeptide was dissolved in a 100 mM sodium phosphate buffer pH 6.5, 0.1% SDS at a protein concentration of 10 mg/ml. The pH value was set to 8.5 by addition of 5 M NaOH and the solution was supplemented with dithiothreitol to a final concentration of 2 mM. The amount of a ruthenium complex activated with a succinimide ester in DMSO that corresponds to the desired offered stoichiometry was added to this solution and it was subsequently incubated for 60 min at 65° C. while stirring. The reaction was terminated by supplementing the reaction mixture with lysine to a final concentration of 10 mM and incubating it for a further 30 min. Subsequently the mixture was dialysed against 100 mM sodium phosphate buffer pH 6.5, 0.1% SDS. The resulting protein solution was admixed with sucrose (final concentration 6.5% (w/v)) and lyophilized in portions.

For the production of a HCV polypeptide derivatized with a ruthenium complex activated with maleinimide, the polypeptide was taken up in 100 mM sodium phosphate buffer pH 6.5, 0.1% SDS (protein concentration 10 mg/ml). An amount of a maleinimide-activated ruthenium complex in DMSO that corresponds to the desired offered stoichiometry was added to this solution and it was incubated for 60 min at 25° C. while stirring. The reaction was terminated by supplementing the reaction mixture with cysteine to a final concentration of 10 mM and further incubating it for 30 min. Afterwards the reaction mixture was dialysed as described above, admixed with sucrose and lyophilized in portions.

Three experiments were carried out in which different ruthenylated antigens were used each time. For experiment A (comparison) the polypeptide was coupled to the ruthenium complex according to EP-A-0 580 979 used as the starting material in examples 1 and 2 in a stoichiometric ratio of 1:3. For experiment B the polypeptide was coupled to the ruthenium complex according to the invention (FIG. 1) produced in example 1 in a stoichiometric ratio of 1:1. For experiment C the polypeptide was coupled to the ruthenium complex (FIG. 3) produced in example 3 in a stoichiometric ratio of 1:1. In all 3 experiments a polypeptide was used as the biotinylated antigen which had been coupled to a maleinimide-activated biotin in a stoichiometric ratio of 1:6. The ruthenylated and biotinylated antigens were in each case used at a concentration of 400 ng/ml test liquid.

The results of experiments A, B and C are shown in Table 2 in ECL counts. It can be seen that a reliable differentiation between a negative serum sample and a critical positive serum sample can only be achieved when using the metal complexes according to the invention with a charged linker as marker groups. This is shown by a higher positive/negative ratio.

TABLE 2

| Experiment | A (comparison) | B | C |
| --- | --- | --- | --- |
| negative sample | 323317 | 132288 | 14467 |
| positive sample | 465769 | 1323338 | 319752 |
| Ratio positive/negative | 1.4 | 10 | 22 |

EXAMPLE 5

Use of metal complexes and biotin groups with a charged linker in immunological tests A double-antigen bridge test was carried out to detect specific antibodies against HIV I according to the protocol of example 4.

The HIV polypeptide gp32 was used as the antigen.

The incorporation of the peptide linker sequences "EEE" and "EEEUZU" between the antigen and the ruthenium complex or/and biotin led to a significant decrease of the unspecific signal compared to antigens without a linker sequence whereas the specific signal was essentially maintained in HIV-positive samples. Thus significantly improved dynamics in the determination of analytes can be achieved by using marker or/and solid phase binding groups with charged linkers.

EXAMPLE 6

Introduction of N-hydroxysuccinimide ester groups into peptide derivatives 250 mg suberic acid-bis-N-hydroxysuccinimide ester (DSS) was dissolved together with 50 µl triethylamine in dimethylformamide. A solution of the peptide derivative BPRu-UEEK (100 mg in DMF) which had been prepared according to the standard method described in example 3 was added dropwise to this. After ca. 15 min the DMF was removed in a high vacuum, the residue was taken up in water and the undissolved DSS was removed by filtration. The filtrate was lyophilized.

The product shown in FIG. 5 was obtained. The purity was 91% according to HPLC. Analysis by means of NMR and MS corresponded to the expected product.

A twice ruthenylated peptide derivative having the sequence Ac-K (BPRu) UEUEUK-(DSS)-UEUEUK (BPRu) UE [SEQ ID NO. 1] was prepared in an analogous manner. Biotinylated peptides or peptides provided with other marker groups or unlabelled peptides can be activated with DSS in an analogous way instead of ruthenylated peptides. Surprisingly the reaction proceeds smoothly in the presence of free carboxylic acid functions.

We claim:
1. A metal complex having the formula:

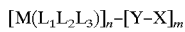

[M(L₁L₂L₃)]ₙ-[Y-X]ₘ wherein
M is a divalent or trivalent metal cation selected from the group consisting of a rare earth metal cation and a transition metal cation;
$L_1$, $L_2$ and $L_3$ are the same or different, and each is a ligand having at least two nitrogen-containing heterocyclic rings, wherein $L_1$, $L_2$ and $L_3$ are bound to the metal cation via nitrogen atoms;
Y is a linker, connected to at least one of $L_1$, $L_2$ and $L_3$, the linker containing at least one charge carrier independently selected from the group consisting of a positive charge carrier and a negative charge carrier;
X is a reactive functional group;
n is 1 to 10; and
m is 1 to 6.

2. The metal complex as claimed in claim 1, wherein M is selected from the group consisting of ruthenium ion, rhenium ion, osmium ion, chromium ion and iridium ion.

3. The metal complex as claimed in claim 1, wherein M is a ruthenium ion.

4. The metal complex as claimed in claim 1, wherein each of $L_1$, $L_2$ and $L_3$ independently contains a ring system selected from the group consisting of bipyridine and phenanthroline.

5. The metal complex as claimed in claim 1, wherein X is selected from the group consisting of carboxylic acid halogenide, carboxylic acid anhydride, active ester, maleimide and a group which is capable of being photo-activated.

6. The metal complex as claimed in claim 1, wherein the metal complex further comprises at least one counterion A which balances the charge carried by the at least one charge carrier.

7. The metal complex as claimed in claim 6, wherein A is at least one group selected from the group consisting of hexafluorophosphate, trifluoroacetate and tetrafluoroborate.

8. The metal complex as claimed in claim 1, wherein Y is a linker containing at least one negative charge carrier selected from the group consisting of phosphate, phosphonate, sulfonate and carboxylate.

9. The metal complex as claimed in claim 1, wherein Y is a linker containing at least one carboxylate group.

10. The metal complex as claimed in claim 1, wherein Y is a linker containing at least one positive charge carrier selected from the group consisting of amino and substituted amino group.

11. The metal complex claimed in claim 10, wherein the at least one positive charge carrier serves as an electron donor for the metal complex.

12. The metal complex as claimed in claim 1, wherein the linker contains 1 to 10 charge carriers.

13. The metal complex as claimed in claim 1, wherein the linker contains 2 to 8 charge carriers.

14. The metal complex as claimed in claim 1, wherein the linker comprises a plurality of aminocarboxylic acid units which are linked together via peptide bonds.

15. The metal complex as claimed in claim 14, wherein the plurality of aminocarboxylic acid units are derived from polyfunctional aminocarboxylic acids which contain at least one free charge carrier after incorporation into the linker.

16. The metal complex as claimed in claim 14, wherein the plurality of aminocarboxylic acid units are derived from trifunctional aminocarboxylic acids which contain (a) one amino group and two carboxylate groups, or
(b) two amino groups and one carboxylate group.

17. The metal complex as claimed in claim 16, wherein the trifunctional aminocarboxylic acids are selected from the group consisting of lysine, ornithine, hydroxylysine, aspartic acid and glutamic acid.

18. The metal complex as claimed in claim 1, wherein the metal complex has the formula:

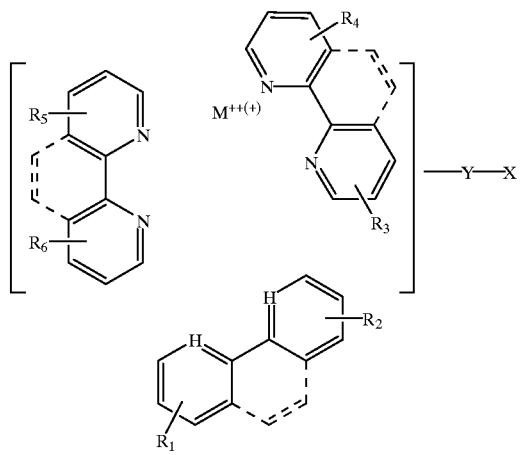

wherein M, Y and X are as stated above; and
$R_1$ through $R_6$, insofar as they are not bound to —Y—X, are each independently selected from the group consisting of hydrogen, $C_1$–$C_5$ alkyl and at least one hydrophilic substituent which is selected from the group consisting of $C_2$–$C_3$ alkyleneoxy, $C_2$–$C_3$ alkylenethio, $C_2$–$C_3$ alkyleneamino, a group of formula —NR—W and a group of formula —O—W, wherein W is an organic residue containing 2 to 10 carbon atoms and 2 to 6 hydroxy groups, and R is hydrogen or $C_1$–$C_5$ alkyl,
wherein at least one of $R_1$ through $R_6$ is bound to —Y—X, and is represented by the formula —(CH₂)ₛ—C(=O)—NH—(CH₂)₂—Y—X, wherein s is 0 to 6.

19. The metal complex as claimed in claim 1, wherein the metal complex has the formula:

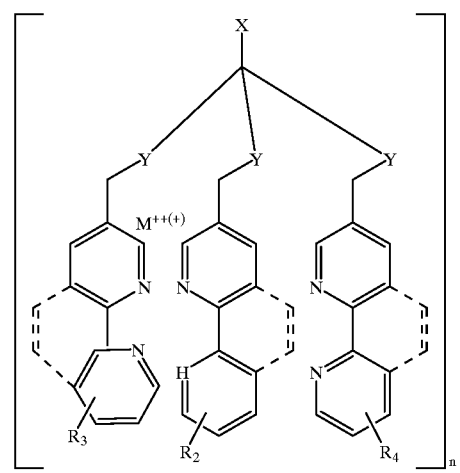

wherein M, Y, X and n are as defined above; and
$R_1$ through $R_3$ are each independently selected from the group consisting of hydrogen, $C_1$–C6 alkyl and at least one hydrophilic group which is selected from the group consisting of $C_2$–$C_3$ alkyleneoxy, C2–$C_3$ alkylenethio, $C_2$–$C_3$ alkyleneamino, a group of formula —NR—W and a group of formula —O—W, wherein W is an organic residue containing 2 to 10 carbon atoms and 2 to 6 hydroxy groups, and R is hydrogen or $C_1$–$C_5$ alkyl.

20. A conjugate, comprising the metal complex as claimed in claim 1 coupled with a biological substance.

21. The conjugate as claimed in claim 20, wherein the biological substance is selected from the group consisting of biotin, an antibody, an antibody fragment, a nucleic acid, a polypeptide antigen, an immunological reactive peptide and a hapten.

22. In an immunological detection method wherein a metal complex is bound to an immunological binding partner and used as a marker group to quantitatively or qualitatively determine an analyte in a sample solution, the improvement comprising using the marker group of claim 1 as the marker group.

23. The method of claim 22, wherein the marker group is determined by luminescence.

24. The method of claim 22, wherein the marker group is determined by electrochemiluminescence.

25. In an immunological detection method wherein a metal complex is bound to an immunological binding partner and used as a marker group to quantitatively or qualitatively determine an analyte in a sample solution, the improvement comprising using the conjugate of claim 20 as the marker group.

26. The method of claim 25, wherein the marker group is determined by luminescence.

27. The method of claim 25, wherein the marker group is determined by electrochemiluminescence.

28. In a nucleic acid hybridization detection method wherein a metal complex is bound to a probe and used as a marker group to quantitatively or qualitatively determine a nucleic acid in a sample solution, the improvement comprising using the marker group of claim 1 as the marker group.

29. The method of claim 28, wherein the marker group is determined by luminescence.

30. The method of claim 28, wherein the marker group is determined by electrochemiluminescence.

31. In a nucleic acid hybridization detection method wherein a metal complex is bound to a probe and used as a marker group to quantitatively or qualitatively determine a nucleic acid in a sample solution, the improvement comprising using the conjugate of claim 20 as the marker group.

32. The method of claim 31, wherein the marker group is determined by luminescence.

33. The method of claim 31, wherein the marker group is determined by electrochemiluminescence.

34. The metal complex as claimed in claim 18, wherein the metal complex further comprises at least one counterion A which balances the charge carried by the at least one charge carrier.

35. The metal complex as claimed in claim 19, wherein the metal complex further comprises at least one counterion A which balances the charge carried by the at least one charge carrier.

* * * * *